United States Patent [19]

Dickens et al.

[11] E Patent Number: Re. 32,711

[45] Reissued Date of Patent: Jul. 12, 1988

[54] ARTERIAL BLOOD FILTER WITH IMPROVED GAS VENTING

[75] Inventors: Duane D. Dickens, San Clemente; Francis M. Servas, San Juan Capistrano, both of Calif.

[73] Assignee: Shiley, Inc., Irvine, Calif.

[21] Appl. No.: 791,376

[22] Filed: Oct. 25, 1985

Related U.S. Patent Documents

Reissue of:

[64] Patent No.: 4,411,783
Issued: Oct. 25, 1983
Appl. No.: 333,832
Filed: Dec. 23, 1981

[51] Int. Cl.[4] ..... B01D 19/00; B01D 27/06; B01D 35/02

[52] U.S. Cl. ..... 210/304; 55/204; 210/436; 210/448; 210/450; 210/472; 210/489; 210/927

[58] Field of Search ..... 55/36, 204–206; 210/94, 188, 304, 349, 436, 441–444, 448, 450, 452, 472, 489, 493.2, 927

[56] References Cited

U.S. PATENT DOCUMENTS

| | | | |
|---|---|---|---|
| 2,010,435 | 8/1935 | Matheson | 210/43 |
| 2,323,525 | 7/1943 | Ebel et al. | 55/205 |
| 3,348,695 | 10/1967 | Rosaen | 210/489 |
| 3,701,433 | 10/1972 | Krakauer et al. | 210/446 X |
| 3,753,336 | 8/1973 | Drew et al. | 242/459 |
| 3,768,653 | 10/1973 | Brumfield | 210/188 |
| 3,771,290 | 11/1973 | Stethem | 55/205 |
| 3,782,083 | 1/1974 | Rosenberg | 210/445 X |
| 3,795,088 | 3/1974 | Esmond | 55/206 |
| 3,822,018 | 7/1974 | Krongos | 210/451 X |
| 3,827,562 | 8/1974 | Esmond | 210/304 |
| 3,849,071 | 11/1974 | Kayser | 23/258.5 |
| 3,939,078 | 2/1976 | Servas et al. | 210/436 |
| 3,996,027 | 12/1976 | Schnell et al. | 55/36 |
| 4,036,616 | 7/1977 | Byrns | 210/493.2 X |
| 4,038,194 | 7/1977 | Luceyk et al. | 210/436 |
| 4,108,778 | 8/1978 | Lambert et al. | 210/297 |
| 4,113,627 | 9/1978 | Leason | 210/446 |
| 4,126,558 | 11/1978 | Luceyk | 210/436 X |
| 4,137,160 | 1/1979 | Ebling et al. | 210/188 X |
| 4,141,835 | 2/1979 | Schael | 210/321 A |
| 4,148,732 | 4/1979 | Burrow et al. | 210/446 X |
| 4,157,965 | 6/1979 | Raible | 210/446 X |
| 4,157,967 | 6/1979 | Meyst et al. | 210/449 |
| 4,164,468 | 8/1979 | Raible | 210/436 X |
| 4,170,056 | 10/1979 | Meyst et al. | 210/446 X |
| 4,187,182 | 2/1980 | Rosenberg | 20/445 |
| 4,303,530 | 12/1981 | Shah et al. | 210/489 X |
| 4,305,825 | 12/1981 | Laval, Jr. | 210/512.1 |
| 4,344,777 | 8/1982 | Siposs | 210/436 X |
| 4,368,118 | 1/1983 | Siposs | 210/136 |
| 4,375,411 | 3/1983 | Wolde-Michael | 210/512.1 |
| 4,490,254 | 12/1984 | Gordon et al. | 210/436 X |

FOREIGN PATENT DOCUMENTS

| | | |
|---|---|---|
| 24601 | 3/1981 | European Pat. Off. . |
| 2041233 | 9/1980 | United Kingdom . |
| 2063108 | 6/1981 | United Kingdom . |

OTHER PUBLICATIONS

"Bentley AF-10 Arterial Filter"; Bentley Laboratories Inc.; two page brochure, copyright 1980.

*Primary Examiner*—Robert Spitzer
*Attorney, Agent, or Firm*—Knobbe, Martens, Olson & Bear

[57] ABSTRACT

A novel liquid filter of the "outside-in" type is disclosed, comprising a hollow tubular housing, a concentrically disposed perforated tubular core surrounded by a cylindrical filter element and communicating with a liquid outlet in the bottom wall of the housing, and a filter element cap covering the upper ends of the perforated core and filter element. A gas vent is located at the highest point in the top wall of the housing, which is at the center of the top wall. The liquid inlet and filter element cap are designed to provide for establishment of a stable swirling flow outside the filter element and above the filter element cap. An improved [means] *way* of bonding upper and lower cup-like portions together to form a hollow tubular housing with high resistance to rupture under pressure is also disclosed. The filter of the invention is particularly suited for use in extracorporeal blood flow circuits, most particularly as an arterial blood filter located downstream from a blood oxygenator.

22 Claims, 1 Drawing Sheet

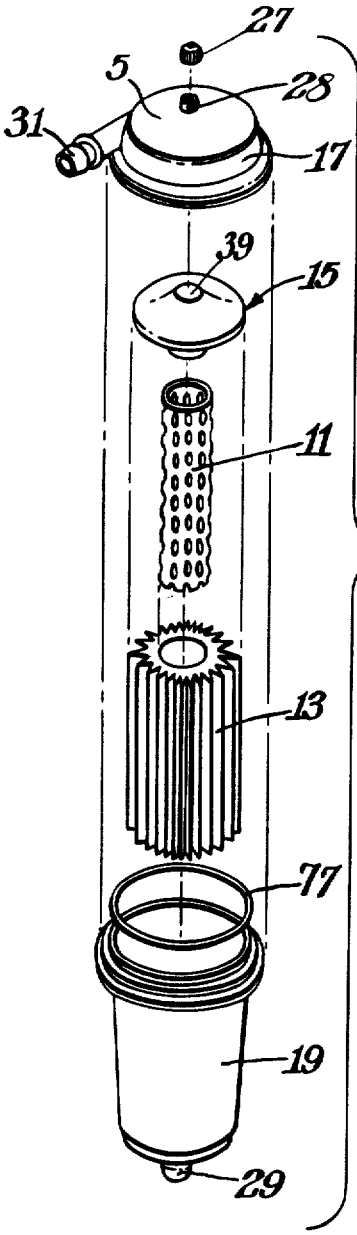
Fig. 1.
Fig. 3.
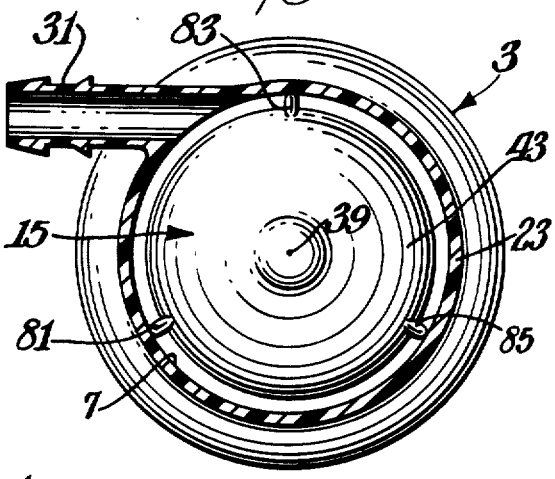
Fig. 2.
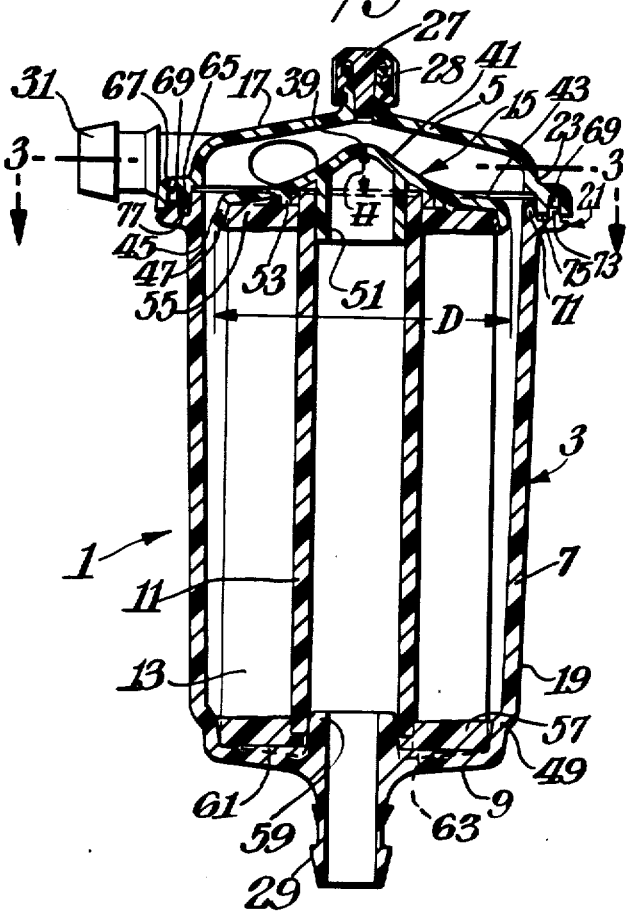
Fig. 4.
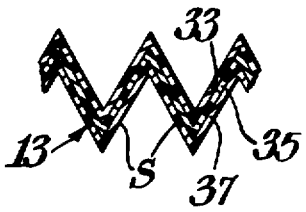

ARTERIAL BLOOD FILTER WITH IMPROVED GAS VENTING

Matter enclosed in heavy brackets [ ] appears in the original patent but forms no part of this reissue specification; matter printed in italics indicates the additions made by reissue.

BACKGROUND OF THE INVENTION

Blood filters are widely used in extracorporeal blood flow circuits, such as those employed in hemodialysis treatments or cardiopulmonary bypass operations (e.g. open heart surgery). These filters are typically disposable, i.e. not resterilized and re-used, and are thus manufactured in mass production from inexpensive materials. In cardiopulmonary bypass circuits, blood filters are usually included both upstream and downstream of a blood oxygenator. An arterial blood filter, located downstream from the oxygenator, is intended to serve a critically important safety function by removing any solid or gaseous emboli, particles, bubbles, etc., that may for example have escaped through the oxygenator or been generated by cavitation behind a pump, from the arterialized blood before it is returned to the patient. Failure to effectively remove such emboli, particles, bubbles, etc., can obviously have disastrous consequences.

As an additional safety factor, an arterial blood filter positioned downstream from a pump must have a very high resistance to rupture under an excessive internal pressurization caused for example by an unexpected blockage of the return line to the patient. In a disposable arterial filter, the high resistance to rupture must be accomplished without markedly raising the cost of manufacture.

One known type of arterial blood filter (see e.g. U.S. Pat. Nos. 3,701,433 and 3,939,078) comprises a hollow tubular housing, an upwardly-extending perforated tubular core concentrically disposed within the housing and surrounded by a cylindrical filter element, e.g. a pleated layer or array of layers wrapped into a cylindrical configuration, a filter element cap covering the upper ends of the perforated core and filter element, a gas vent in the top wall of the housing, a blood inlet in communication with the space between the filter element and the side wall of the housing, and a blood outlet in communication with the space within the perforated core. The flow of blood through the cylindrical filter element is substantially radial, from the outside of the cylindrical element to the inside thereof. Although this known type of arterial blood filter has been used for many years with considerable benefit to mankind, it is nevertheless in need of improvement. The input blood upstream of the filter element tends to develop regions of churning flow, which interfere with the orderly passage of gaseous emboli and bubbles to the vent. As a result, one must rely excessively upon the layer in the filter element having the smallest pore size, e.g. a woven filter screen, to prevent the passage of gaseous emboli and bubbles through the filter element and to the patient. Consequently, the probability of such passage occurring is higher than if a smooth orderly gas venting were provided. Furthermore, the development of regions of churning flow may give rise to excessive destruction of blood components.

SUMMARY OF THE INVENTION

It is an object of the present invention to provide a disposable blood filter, suitable for use in an extracorporeal blood flow circuit, in which gas bubbles and gaseous emboli in the blood input are vented in a highly predictable manner along orderly pathways. This and other objects of the invention are achieved with a novel liquid filter, suitable for use in an extracorporeal blood flow circuit, comprising a hollow tubular housing having a side wall, a top wall having a highest point at the center thereof and a bottom wall, a perforated tubular core concentrically disposed within said housing, a cylindrical filter element surrounding said core and displaced from said side wall, a filter element cap covering the upper ends of said core and said filter element and displaced from said top wall, a gas vent in said top wall at said highest point, a substantially horizontal liquid inlet in said side wall adjacent said top wall, and a filtrate outlet in said bottom wall of said housing in communication with the space within said core, with the upper surface of said filter element cap being symmetrical about the longitudinal axis of said housing, having a highest point at its center, and being without any points of localized minimum height, and with said inlet being adapted to direct the incoming flow of liquid in a nonperpendicular manner against the side wall of the housing, whereby a swirling flow of liquid is established outside said filter element and above said filter element cap. The establishment of a swirling flow or vortex creates a negative pressure gradient in all direction towards the centrally located vented, thereby providing orderly pathways for the movement of gaseous emboli and gas bubbles in the input liquid to the vent.

In a preferred embodiment of the novel filter, the upper surface of the filter element cap includes a generally conical central portion generally overlying the perforated tubular core, and a relatively flat peripheral portion surrounding said central portion.

The cylindrical filter element preferably comprises an array of layers, with said array being provided with a plurality of longitudinal pleats and wrapped into a cylindrical configuration. More preferably, the array consists of three layers, a woven screen middle layer of synthetic polymeric filaments having a pore size of from about 15 microns to about 50 microns and identical inner and outer supporting sheets of open mesh extruded synthetic polymeric netting of much greater pore size. In one embodiment of the novel filter, an array of layers comprising the filter element is provided with not more than about 12 longitudinal pleats per inch of outer circumference of the perforated tubular core and includes an woven screen of synthetic polymeric monofilaments having a pore size of from about 15 microns to about 25 microns. In this embodiment, the small pore size woven screen provides an optimal barrier against passage of gaseous emboli, while the relatively open pleat configuration eliminates the risk of capturing gaseous emboli between pleats and provides for the ready and easy priming of the filter.

Another aspect of a novel filter of the invention relates to the manner in which upper and lower mating cup-like portions are bonded together at a seam to form a hollow tubular housing having an excellent resistance to rupture at the seam under excessive internal pressurization.

DETAILED DESCRIPTION OF THE INVENTION

The invention will be described in detail with reference to a preferred embodiment thereof, which is a disposable arterial blood filter for use in an extracorporeal blood flow circuit including a blood oxygenator. Reference to this embodiment does not limit the scope of the invention, which is limited only by the scope of the claims.

In the drawings:

FIG. 1 is an exploded perspective view of an arterial blood filter of the invention;

FIG. 2 is a longitudinal sectional view of the filter of FIG. 1;

FIG. 3 is a sectional view along line 3—3 in FIG. 2; and

FIG. 4 is a transverse sectional view through a portion of the filter element of the filter of FIG. 1.

A disposable blood filter 1 of the invention is shown in FIGS. 1 and 2. It is an arterial blood filter, i.e. suitable to be included in an extracorporeal blood flow circuit downstream of a blood oxygenator. Filter 1 comprises a hollow tubular housing 3 having a top wall 5, side wall 7 and bottom wall 9, a vertically-extending perforated tubular core 11 concentrically disposed within housing 3, a cylindrical filter element 13 surrounding and supported by tubular core 11, and a filter element cap 15 covering the upper ends of tubular core 11 and filter element 13. Tubular housing 3 is formed from cup-like upper and lower portions 17 and 19 secured together in a manner to be described below at seam 21. Side wall 7 of housing 3 extends upwardly to include the short vertically-extending portion 23 of upper portion 17. Top wall 5 of tubular housing 3 is upwardly inclined continuously from its circumferential perimeter to a highest point at the center of the wall, at which highest point gas vent 28 is located. Gas vent 28 comprises a Luer fitting. Filter 1 also includes outlet 29 in bottom wall 9, which communicates with the interior of tubular core 11, and horizontal inlet 31 in side wall 3 adjacent top wall 5. The downwardly-extending annular rim 45 of filter element cap 15 terminates at edge 47, which is bevelled (see FIG. 2) so that gas bubbles and gaseous emboli cannot be trapped beneath it. Lower portion 19 is slightly tapered (see FIG. 2), for reasons that will be explained below.

Cylindrical filter element 13 is shown in FIG. 1 and, in a transverse sectional view, FIG. 4. It comprises an array of three superimposed layers 33, 35 and 37 folded together in a plurality of longitudinal pleats and wrapped into a cylindrical configuration with opposed ends sealed at a seam by conventional means. Middle layer 35, the principal filtering layer, is a woven screen of nylon filaments having a pore size of about 20 microns. (In another preferred embodiment of the invention, woven nylon screen 35 has a pore size of about 40 microns.) Identical layers 33 and 37 of either side of screen 35 are made of extruded open mesh polypropylene netting having a pore size of about 100 microns. Layers 33 and 37 serve to support screen 35 against collapse at the substantial flow rates experienced during operation of the arterial filter 1. Additionally, the upstream open mesh layer serves to trap any solid debris that may be present in the blood. The layers in the array may be rendered hydrophilic by treatment with a wetting agent, for example, a hydrophilic non-ionic polyethylene oxide homopolymer such as a Polyox resin (Union Carbide Corp., New York, N.Y.), a blood-compatible surfactant or a purified plasma protein such as heparin or albumin. Cylindrical filter element 13 preferably has an open pleat configuration in use. That is, a substantial space S (see FIG. 4) is left between adjacent pleats. Thus, as one example only, filter element 13 may be provided with 29 longitudinal pleats evenly distributed along a 2.64 inch circumference (corresponding to a 0.84 inch diameter) of the outer surface of perforated core 11. The advantages of the open pleat filter element configuration are discussed above.

Of critical importance to the present invention is the design of filter element cap 15. The upper surface of cap 15 is symmetrical about the longitudinal axis of tubular housing 3 and has its highest point 39 at its center. The assembly of core 11, filter element 13 and cap 15 is positively fixed symmetrically with respect to the longitudinal axis of housing 3 by means of three evenly circumferentially distributed spacers 81, 83 and 85 provided in the cap 15, each of which contacts an adjacent portion of side wall 7 of housing 3 in the region of seam 21. Furthermore, there are no localized points or regions of minimum height (i.e., dimples, grooves, valleys, etc.) upon the upper surface of cap 15. The upper surface of the filter element cap may be continuously inclined from its perimeter to its center point or, alternatively, its peripheral portion may be completely flat. Preferably, as shown in FIG. 2, said upper surface includes a generally conical central portion 41 generally overlying tubular core 11, and a relatively flat peripheral portion 43 surrounding central portion 41. More preferably, the ratio of the height H of the upper surface of cap 15 to the diameter D of said surface (see FIG. 2) is from about 0.10 to about 0.25 and said height is greater than the distance between point 39 and vent 28. Other designs for the upper surface of cap 15 are possible. Thus, as only one additional example, said surface may include a generically hemispherical central portion generally overlying the perforated tubular core, and a relatively flat peripheral portion.

As is shown in FIGS. 1 to 3, horizontal inlet 31 is so situated that the input blood does not directly impinge on cap 15 or element 13, but instead first contacts, in a non-perpendicular manner, the inner surface of side wall 7 of housing 3. In the filter shown in FIGS. 1 to 3, the input blood contacts side wall 7 at an acute angle. Other designs are possible in which the input blood contacts the side wall in an essentially tangential manner.

The net effect of the configuration of elements in filter 1, particularly filter element cap 15 and inlet 31, is the establishment over a wide range of blood throughput flow rates of a stable swirling flow of blood, i.e. a vortex, between filter element 13 and side wall 7 and between filter element cap 15 and top wall 5. As a consequence, a negative pressure gradient towards the vent, which provides the driving force for gas bubble and gaseous emboli removal, exists throughout the swirling blood. This negative pressure gradient creates an orderly system of pathways for gas bubble and gaseous emboli removal at the centrally located vent 28. The input stream of blood through inlet 31 is directed away from vent 28 and thus does not interfere with the venting.

In operation as an arterial blood filter in an extracorporeal blood flow circuit including a blood oxygenator, inlet 31 is connected to a line leading from the oxygenator, outlet 29 is connected to a line leading to the patient, Luer cap 27 is removed from Luer fitting 28, a stopcock (not shown) is installed on fitting 28 and the stopcock is connected to a vent line leading to a non-pressurized port on the blood oxygenator or a cardiotomy reservoir. The extracorporeal circuit is primed with saline solution before the circulation of the patient's blood through it commences. The stopcock installed on fitting 28 is in the open position during filtration of the patient's blood but must be closed prior to stopping the extracorporeal circuit pump to prevent backflow of blood in the filter. During steady-state filtration, the entire space within housing 3 above filter element cap 15 is filled with the patient's blood.

As one example only of the filter 1 shown in FIGS. 1 to 4, filter element 13 is provided with 29 longitudinal pleats evenly distributed along the outer circumference of perforated tube 11, tube 11 has an outer diameter of 0.84 inch, H is 0.35 inch and D is 2.035 inches. The average inner diameter of side wall 7 between rounded shoulder 49 and seam 21 is 2.18 inches. In a filter 1 of the invention having these dimensions, excellent results are obtained at blood throughput flow rates of from about 1 liter/minute to about 6 liters/minute.

Filter 1 is manufactured by conventional methods. Upper cup-like portion 17, is prepared as a single piece including inlet 31 and fitting 28. Lower cup-like portion 19 is prepared as a single piece including outlet 29. Portions 17 and 19, as well as cap 15, are made of an inexpensive clear plastic material, preferably a thermoplastic such as a polycarbonate, while core 11 is also made of an inexpensive plastic material, preferably polypropylene. The slight upward/outward taper of lower portion 19 results from its manufactured by injection molding, which is preferred because of its low cost. This taper is beneficial to the function of the filter since it acts to equalize the pressure gradient across filter element 13 at different longitudinally displaced locations.

In assembling the filter, filter element cap 15 is first held upside down and filled, between tubular projection 51 and rim 45, with a hot melt adhesive 55 such as ethylene vinyl acetate. Perforated core 11 (carrying filter element 13) is then lowered onto cap 15. Core 11 loosely receives projection 51, which filter element 13 rests upon annular flange 53 of cap 15 and fits loosely within rim 45. Core 11 (carrying filter element 13) and cap 15 are held together in their desired perpendicular relative configuration by a suitable fixture (not shown). After adhesive 55 has hardened, the resulting assembly is removed from the fixture holding it. Lower cup-like portion 19 is filled with a hot melt adhesive 57, e.g. ethylene vinyl actate, between tubular projection 59 and side wall 7 below shoulder 49. The assembly of core 11, filter element 13 and cap 15 is then lowered onto lower portion 19, with core 11 loosely receiving projection 59 and filter element 13 fitting loosely within side wall 7 below shoulder 49. Filter element 13 rests upon a substantial number, for example twenty-four, of equally distributed radially-extending ribs e.g. 61, 63, in single piece construction with portion 19 and extending upwardly from slightly inclined lower wall 9. Provision of these ribs improves the bonding of filter element 13 to lower portion 19. The assembly of core 11, filter element 13 and cap 15 is held together with lower portion 19 in the desired concentric relative configuration by a suitable fixture (not shown). After adhesive 57 had hardened, the resulting assembly is removed from the fixture holding it.

As can be seen in FIG. 2, upper cup-like portion 17 contains inner and outer downwardly-extending annular rims 65 and 67 defining annular groove 69 between them, while lower cup-like portion 19 contains inner and outer upwardly-extending annular rims 71 and 73 defining annular groove 75 between them. A silicone rubber "O"-ring 77 is held within groove 75. Portion 17 and 19 are adapted to be joined together, thereby forming seam 21, with rim 73 received within groove 69 and rim 65 received within groove 75. After such joining has been accomplished, rim 73 is bonded to rim 67 and to rim 65, preferably by ultrasonic bonding, with portions 17 and 19 held under compression so that ring 77 is compressed within groove 75. Gaps are left between rims 73 and 65 and the bases of grooves 69 and 75, respectively. The result is a triple hermetic seal between portions 17 and 19. The double shear seal provided by the bonding of rim 73 to rims 65 and 67 imparts an excellent burst resistance to seam 21 of filter 1; internal pressures far in excess of 50 psi can be tolerated without bursting. If desired, a triple shear seal may be provided by additionally bonding rim 71 to rim 65.

After the bonding of upper portion 17 to lower portion 19 is completed, Luer cap 27 is installed on Luer fitting 28 and plastic protective caps are placed over inlet 31 and outlet 29. The filter is then sterilized and packaged in a sterile condition, e.g. in a clear plastic peel-open pouch, for distribution to the ultimate user, who disposes it after a single use.

We claim:

1. A liquid filter suitable for use in an extracorporeal blood flow circuit comprising a hollow tubular housing having a side wall, a top wall having a highest point at the center thereof and a bottom wall, a gas vent in said top wall at said highest point, a perforated tubular core concentrically disposed within said housing, a cylindrical filter element surrounding said core and displaced from said side wall, a filter element cap covering the upper ends of said core and said filter element and displaced from said top wall, a substantially horizontal liquid inlet in said side wall adjacent said top wall, and a filtrate outlet in said bottom wall of said housing in communication with the space within said core, with the upper surface of said filter element cap being symmetrical about the longitudinal axis of said housing, having a highest point at its center, and being without any points of localized minimum height, and with said inlet being adapted to direct the incoming flow of liquid in a non-perpendicular manner against the side wall of said housing, whereby a swirling flow of liquid is established outside said filter element and above said filter element cap.

2. A filter of claim 1 wherein said upper surface of said filter element cap is continuously inclined from the perimeter to the center of said cap.

3. A filter of claim 1 or 2 wherein said upper surface includes a generally conical central portion generally overlying said perforated tubular core, and a relatively flat peripheral portion surrounding said central portion and generally overlying said filter element.

4. A filter of claim 3 wherein the ratio of the height of said upper surface to the diameter of said upper surface is from about 0.10 to about 0.25.

5. A filter of claim 4 wherein said height is greater than the distance between said highest point at the center of the filter element cap and said gas vent.

6. A filter of claim 1 wherein said filter element comprises an array of layers, with said array being provided with a plurality of longitudinal pleats.

7. A filter of claim 6 wherein one of said layers is a woven screen of synthetic polymeric monofilaments having a pore size of from about 15 microns to about 50 microns.

8. A filter of claim 7 wherein said array is provided with not more than about 12 longitudinal pleats per inch of outer circumference of said perforated tubular core.

9. A filter of claim 8 wherein one of said layers is a woven screen of synthetic polymeric monofilaments having a pore size of not more than about 25 microns.

10. A filter of claim 6 wherein at least one of said layers has been rendered hydrophilic by treatment with a wetting agent.

[11. In a hollow tubular housing comprising a plastic upper cup-like portion having a top wall, a downwardly-extending side wall and an open bottom end, secured to a plastic lower cup-like portion having a bottom wall, an upwardly-extending side wall and an open top end, the improvement wherein the lowermost portion of said upper portion includes inner and outer downwardly-extending annular rims defining a first annular groove between them, the uppermost portion of said lower portion includes inner and outer upwardly-extending annular rims defining a second annular groove between them, with said outer annular rim of said lower portion received within said first annular groove so as to leave a gap between said outer annular rim and the base of said first annular groove and with said inner annular rim of said upper portion received within said second annular groove so as to leave a gap between said inner annular rim and the base of said second annular groove, said two outer annular rims are bonded together by ultrasonic bonding and said outer upwardly-extending annular rim is bonded to said inner downwardly-extending annular rim by ultrasonic bonding, whereby a double shear seal capable of withstanding elevated pressure is obtained.]

[12. The improvement of claim 11 wherein additionally said two inner annular rims are bonded together by ultrasonic bonding, whereby a triple shear seal is obtained.]

[13. The improvement of claim 11 wherein additionally a compressible circular silicone rubber ring is held in a compressed state within said gap between the inner annular rim of said upper portion and the base of said second annular groove.]

*14. A filter of claim 3 wherein the height of said upper surface is greater than the distance between said highest point at the center of the filter element cap and said gas vent.*

*15. A liquid filter suitable for use in an extracorporeal blood flow circuit comprising:*

*a hollow tubular housing having a side wall, a top wall having a highest point at the center thereof and a bottom wall;*

*a gas vent in said top wall at said highest point;*

*an annular filter element concentrically disposed within said housing and displaced from said side wall,*

*means to support said filter element within said housing while permitting liquid flow in a substantially radial direction through said filter element,*

*a filter element cap covering the upper end of said filter element and displaced from said top wall,*

*a substantially horizontal liquid inlet in said side wall adjacent said top wall, and*

*a filtrate outlet in said bottom wall of said housing in communication with the inner space within said annular filter element,*

*with the upper surface of said filter element cap being symmetrical about the longitudinal axis of said housing, having a highest point at its center, and being without any points of localized minimum height, and with said inlet being adapted to direct the incoming flow of liquid in a non-perpendicular manner against the side wall of said housing,*

*whereby a swirling flow of liquid is established outside said filter element and above said filter element cap.*

*16. A filter of claim 15 wherein said upper surface of said filter element cap is continuously inclined from the perimeter to the center of said cap.*

*17. A filter of claim 15 or 16 wherein said upper surface includes a generally conical central portion generally overlying the inner space within said filter element, and a relatively flat peripheral portion surrounding said central portion and generally overlying said filter element.*

*18. A filter of claim 17 wherein the ratio of the height of said upper surface to the diameter of said upper surface is from about 0.10 to about 0.25.*

*19. A filter of claim 18 wherein said height is greater than the distance between said highest point at the center of the filter element cap and said gas vent.*

*20. A filter of claim 15 wherein said filter element comprises an array of layers, with said array being provided with a plurality of longitudinal pleats.*

*21. A filter of claim 20 wherein one of said layers is a woven screen of synthetic polymeric monofilaments having a pore size of from about 15 microns to about 50 microns.*

*22. A filter of claim 21 wherein said array is provided with not more than about 12 longitudinal pleats per inch of inner circumference of said filter element.*

*23. A filter of claim 22 wherein one of said layers is a woven screen of synthetic polymeric monofilaments having a pore size of not more than about 25 microns.*

*24. A filter of claim 20 wherein at least one of said layers has been rendered hydrophilic by treatment with a wetting agent.*

*25. A filter of claim 17 wherein the height of said upper surface is greater than the distance between said highest point at the center of the filter element cap and said gas vent.*

* * * * *